(12) United States Patent
Fouquet

(10) Patent No.: US 7,224,468 B2
(45) Date of Patent: May 29, 2007

(54) EN-FACE FUNCTIONAL IMAGING USING MULTIPLE WAVELENGTHS

(75) Inventor: Julie Elizabeth Fouquet, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 451 days.

(21) Appl. No.: 10/690,046

(22) Filed: Oct. 20, 2003

(65) Prior Publication Data

US 2005/0083536 A1    Apr. 21, 2005

(51) Int. Cl.
*G01B 9/02*    (2006.01)

(52) U.S. Cl. .................................................... 356/497

(58) Field of Classification Search ............... 356/497, 356/479
See application file for complete search history.

(56) References Cited

U.S. PATENT DOCUMENTS

| 4,806,776 | A |   | 2/1989  | Kley |
| 5,450,205 | A | * | 9/1995  | Sawin et al. ................. 356/632 |
| 6,485,413 | B1 |   | 11/2002 | Boppart et al. |
| 6,611,339 | B1 | * | 8/2003  | Yang et al. ................. 356/485 |
| 6,847,454 | B2 | * | 1/2005  | Crowley et al. ............ 356/479 |
| 2003/0137669 | A1 |   | 7/2003  | Rollins et al. |

FOREIGN PATENT DOCUMENTS

WO    WO 97/32182    2/1997

* cited by examiner

*Primary Examiner*—Hwa (Andrew) Lee (57) ABSTRACT

Methods and apparatus for en-face imaging using multiple wavelengths are described. In general, an imaging system receives light reflected from a sample under test and distinguishes between reflected light at a first wavelength and reflected light at a second wavelength. Images at both wavelengths are collected simultaneously. En-face images are output using en-face image data corresponding to the first wavelength and en-face image data corresponding to the second wavelength.

21 Claims, 4 Drawing Sheets

EN-FACE FUNCTIONAL IMAGING USING MULTIPLE WAVELENGTHS

TECHNICAL FIELD

Embodiments in accordance with the invention generally relate to the field of imaging. More specifically, embodiments in accordance with the invention pertain to functional imaging.

BACKGROUND ART

Functional imaging is a term of art that in general refers to techniques in which the aim is to extract quantitative information about physiological function from image-based data. Optical coherence tomography (OCT) is an imaging modality that can resolve much smaller features than ultrasound, and overcomes issues associated with the scatter of visible and near-visible light in human tissue that make other forms of optical imaging quite difficult.

Figure 1:
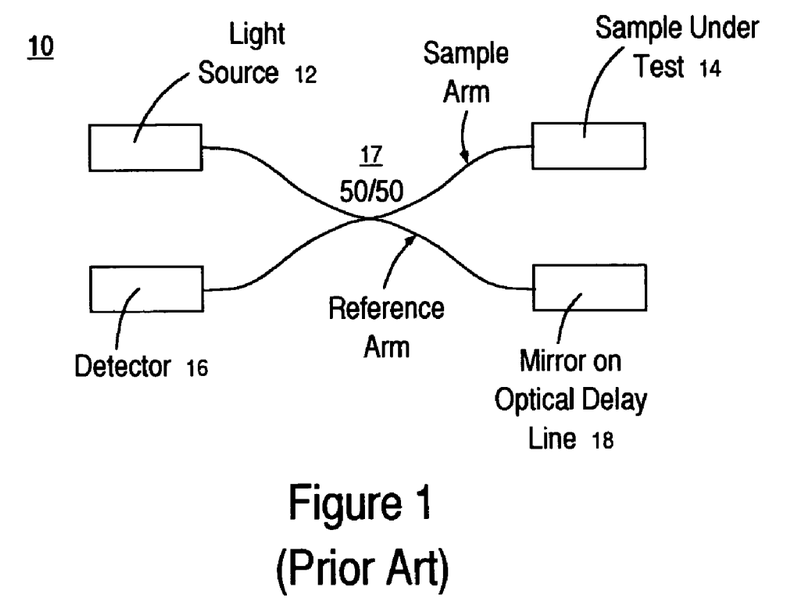
FIG. 1 is a block diagram of a prior art apparatus for collecting image data.

In conventional fiber-based OCT, an interferometer is used to collect image data of a sample under test. FIG. 1 is a block diagram of a prior art apparatus 10 that exemplifies a Michelson interferometer. Light from light source 12 travels through a single-mode optical fiber to beam splitter 17, typically a 50/50 beam splitter. Beam splitter 17 directs a portion of the light along a single-mode optical fiber sample arm to the sample under test 14, with the remainder of the light directed along a single-mode optical fiber reference arm to the mirror 18. Sample under test 14 is, for example, a fiber-optic device or human tissue. The delay line with a mirror 18 increases the optical length of the reference arm. By moving the mirror back and forth, reflection data can be collected at different depths within sample under test 14. Light reflected from sample under test 14 is received by photon detector 16, as is light reflected from the moveable mirror 18. Photon detector 16 has just one spatial channel (that is, a single large pixel).

To obtain an image, the sample arm optical fiber is placed at a location in (or on) the sample. A depth scan is obtained at that location. The optical fiber is then moved to an adjacent location and another depth scan is obtained. The process is repeated laterally across the sample, with a depth scan performed at each lateral location. A scan of one line can be referred to as a transverse scan. To create a two-dimensional image of a sample, transverse scans are performed over the area of the sample.

The process of performing depth scans and transverse scans on a sample can be time-consuming. If each depth scan takes 0.01 seconds and 1000×1000 depth scans are performed across the area of the sample, then approximately three hours are needed to complete the measurements.

En-face imaging with a free-space reflectometer and lamp source provides an approach for speeding up the collection of information. En-face images are planar images of the sample, captured simultaneously using parallel optical channels in the sample arm of a device like apparatus 10. In this case, the beam splitter may be a bulk optic free space beam splitter, and the optical signals may propagate in free space within some or all of the arms rather than in optical fibers. Moving the location of the reflector in the reference arm changes the optical depth at which image information is collected. Image information can be collected in two dimensions simultaneously and thus more rapidly. However, lateral scatter of photons from adjacent sample locations can reduce contrast. Thus, en-face imaging, while speeding up image collection, can reduce image quality.

Accordingly, a functional imaging system and/or method that addresses the problems described above would be of value.

SUMMARY OF THE INVENTION

The invention provides, in various embodiments, methods and apparatus for en-face imaging using multiple wavelengths. In general, an imaging system receives light reflected from a sample under test and distinguishes between reflected light at a first wavelength and reflected light at a second wavelength. The imaging system can include first regions for detecting light of a first wavelength while blocking light of a second wavelength and second regions for detecting light of the second wavelength. Each of the first and second regions may correspond to a respective pixel of a single imager, interleaved in a pattern. Alternatively, the first regions may be part of a first imager and the second regions may be part of a second imager. Images at both wavelengths are collected simultaneously.

En-face images are output using en-face image data corresponding to the first wavelength and en-face image data corresponding to the second wavelength. En-face images can be collected with higher contrast by, for example, taking the difference between the en-face image corresponding to the first wavelength and the en-face image data corresponding to the second wavelength.

BRIEF DESCRIPTION OF THE DRAWINGS

The accompanying drawings, which are incorporated in and form a part of this specification, illustrate embodiments in accordance with the invention and, together with the description, serve to explain the principles of the invention. The drawings referred to in this description should not be understood as being drawn to scale except if specifically noted.

DETAILED DESCRIPTION OF THE INVENTION

Reference will now be made in detail to the various embodiments in accordance with the invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. In other instances, well-known methods, procedures, components, and circuits have not been described in detail as not to unnecessarily obscure aspects of the present invention.

Figure 2:
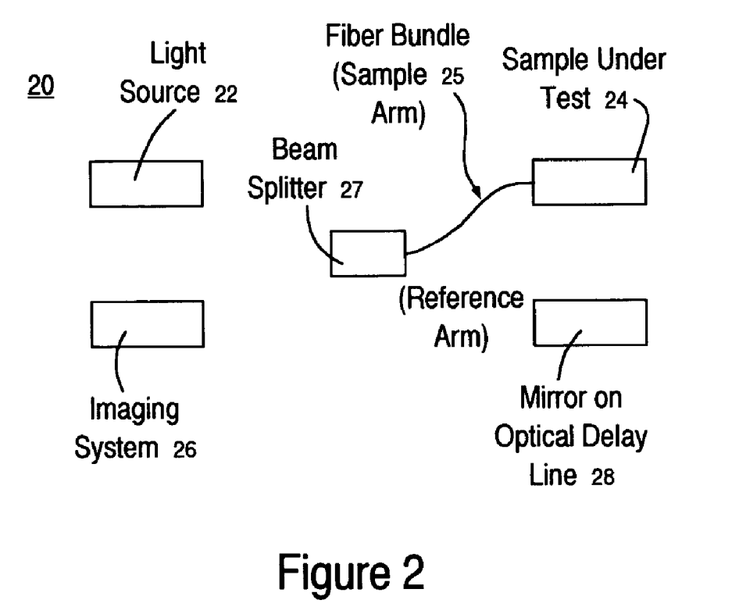
FIG. 2 is a block diagram of one embodiment of an en-face imaging system in accordance with the invention.

FIG. 2 is a block diagram of an apparatus 20 for en-face imaging of a sample under test 24 using multiple wavelengths of light in one embodiment in accordance with the invention. En-face images are planar images of the sample, captured simultaneously. En-face image data can be thought of as representing the image generated at a two-dimensional plane that intersects the sample under test 24.

In the embodiment of FIG. 2, apparatus 20 includes a light source 22, an imaging system 26, a beam splitter 27, and a mirror on an optical delay line 28. Apparatus 20 includes or is coupled to an imaging system 26. Apparatus 20 can include other elements in addition to those discussed herein.

Aspects of apparatus 20 (e.g., light source 22, beam splitter 27 and mirror on optical delay line 28) can be implemented in a reflectometer or an interferometer such as a Michelson interferometer. An overview of these elements (e.g., light source 22, a beam splitter 27 and mirror on optical delay line 28) is provided below; however, more detailed descriptions of the elements and the operation of an interferometer are not provided, as the principles and features of interferometers are well known in the art.

Light source 22 is an incoherent light source that transmits light at two or more different wavelengths. In one embodiment, light source 22 includes a source of white light in combination with a diffuser, as this provides an inexpensive source of incoherent light relative to other types of light sources. Use of a white light source may engender the use of filter(s) to eliminate or block wavelengths other than the wavelengths selected for use; refer to FIG. 8. Other types of lights sources, such as edge emitting light emitting diodes (EELEDs) or low coherence superluminescent light emitting diodes (SLDs), can be used. Light source 22 can include an aiming beam. Also, multiple light sources can be used. Multiple light sources can be combined using beam splitters, fiber combiners, or by focusing one source to transmit through another.

In the embodiment of FIG. 2, light from light source 22 travels through free space to beam splitter 27. In one embodiment, beam splitter 27 is a 50/50 beam splitter. In general, beam splitter 27 functions to direct some portion of the light from light source 22 to the sample under test 24, allowing the remainder of the light to pass in free space along the reference arm to the mirror on optical delay line 28. It is appreciated that the function provided by beam splitter 27 can be performed using other mechanisms.

In the present embodiment, one or more compact and coherent optical fiber bundles 25, having small diameters on the order of a few millimeters, are used to carry light from beam splitter 27 to the sample under test 24. When multiple fiber bundles are used in the interferometer, the rotation angles between the input and output ends of each of the fiber bundles, the positions of the fibers within the bundles, as well as the magnification in the reference and sample arms, are matched in order to properly register the images collected by each bundle.

Because the cladding around each core in a fiber bundle occupies a significant fraction of the bundle's cross-section, the fiber cores can sample only an array of spots on the sample under test 24. Lateral (or transverse) scanning can be used to scan the cores over the remaining regions of the sample under test. While this image capture process will take longer than the single depth scan of a fully bulk en face reflectometer, it is not nearly as slow as using a single fiber to scan the sample because the extent of the scan translations are limited to the spacing between adjacent fibers.

Sample under test 24 can be, but is not limited to, a device or human tissue. In the latter case, sample under test 24 can be in vivo or in vitro. For example, in vivo measurements can be performed in conjunction with the coherent optical fiber bundle(s) just described.

The mirror on optical delay line 28 increases the optical length of the reference arm, thereby increasing the amount of time needed for light to traverse the length of the reference arm. Through manipulation of the mirror on optical delay line 28 (for example, by moving the mirror back and forth to increase the optical length of the reference arm), reflection data can be collected at different depths within sample under test 24.

Imaging system 26 generally includes one or more imagers for receiving incident light reflected from the sample under test 24 and for receiving incident light from mirror on optical delay line 28. In general, imaging system 26 functions to generate en-face image data from the two (or more) wavelengths contained in the incident light. In the embodiment of FIG. 2, light reflected from sample under test 24 and mirror on optical delay line 28 travels in free space from the beam splitter 27 to imaging system 26.

The imager(s) of imaging system 26 can utilize, for example, a charge-coupled device (CCD) imager or a complementary metal-oxide semiconductor (CMOS) imager. Imaging system 26 can include other elements, such as but not limited to circuitry and other electronics related to the imaging system, processing capability for processing the image data, display capability for displaying images, storage capability for storing image data or images, and electronics for data transfer. As will be seen, imaging system 26 can also include filter(s) to eliminate wavelengths other than the wavelengths selected for use.

It is appreciated that, in alternate embodiments, some or all of the free space portions of apparatus 20 are instead fiber-based. When one or more coherent fiber bundles are used, light reflected from sample under test 24 can be passed through a beam splitter before it reaches the imaging system 26.

The image data are collected at two (or more) wavelengths. As will be described, imaging system 26 is configured to distinguish between each of the different wavelengths in use, in order to generate high contrast en-face images of the sample under test 24. The wavelengths can be selected to augment the contrast in en-face images of the sample under test 24. For example, one wavelength may more readily detect oxyhemoglobin (hemoglobin with bound oxygen) while another wavelength may more readily detect hemoglobin without bound oxygen. An en-face image generated using these two wavelengths will include greater contrast between regions of comparatively better or worse blood oxygenation and/or perfusion.

Figure 3:
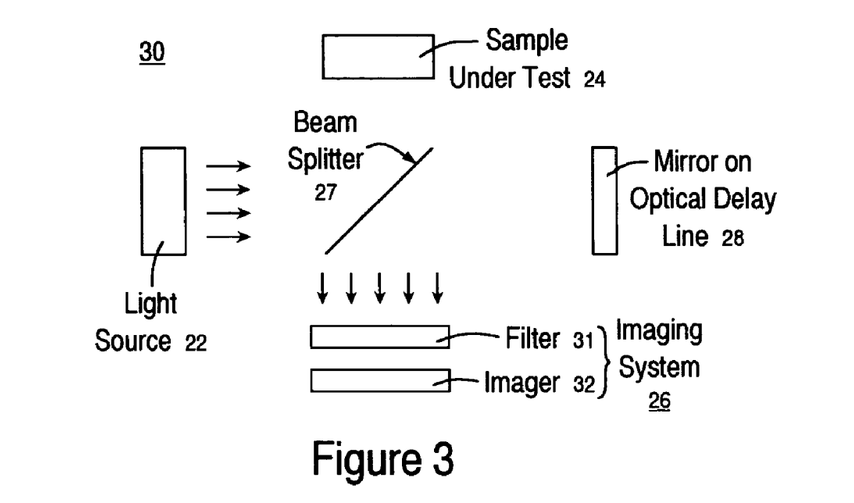
FIG. 3 is a block diagram of a second embodiment of an en-face imaging system in accordance with the invention.

FIG. 3 is a block diagram of an apparatus 30 for en-face imaging in an embodiment in accordance with the invention.

The imaging system 26 of apparatus 30 includes an imager 32 that is configured to collect image information at two (or more) wavelengths. In one embodiment, a bulk or large area filter 31 is situated to intercept incident light before the light reaches the imager 32. In an alternate embodiment, filter 31 is positioned to intercept light as the light is emitted from light source 22. Although a single bulk filter is shown, the invention is not so limited; for example, multiple bulk filters can be used in series. Imager 32 is described further in conjunction with FIG. 7, and filter 31 is described further in conjunction with FIG. 8.

In operation, apparatus 30 of FIG. 3 functions as follows for an example based on two wavelengths; however, the invention is not so limited. Light source 22 generates light having a range of wavelengths including a first wavelength and a second wavelength. The first and second wavelengths are selectable, as described above. The light may be filtered by an optional bulk filter as it is transmitted from light source 22 (e.g., a bulk filter such as that described by FIG. 8). A portion of the light from light source 22 is directed to sample under test 24 by beam splitter 27, and the remainder of the light is passed to mirror on optical delay line 28. The light is essentially broadcast to the sample under test 24 and the mirror on optical delay line 28.

Continuing with reference to FIG. 3, light reflected from the sample under test 24 is received by imager 32. The reflected light may be filtered by the optional filter 31 before the light reaches imager 32. Imager 32 distinguishes between reflected light at the first wavelength and reflected light at the second wavelength, as described further in conjunction with FIG. 7. Image data corresponding to the first wavelength and image data corresponding to the second wavelength can be used to generate one or more en-face images. For example, separate en-face images may be generated corresponding to the different wavelengths, or a single en-face image may be generated based on the combination of the image data (for example, as described below, image data may be differenced). Mirror on optical delay line 28 can then be used to increase the optical length of the reference arm (e.g., a mirror can be moved to a different position), and the process is repeated to generate en-face images at different depths of sample under test 24.

The discussion above describes an embodiment in which light travels in free space. As mentioned previously herein, all or some of the free space portions of apparatus 30 can instead be fiber-based. In one embodiment, with reference to FIGS. 2 and 3, light from beam splitter 27 is transmitted through fiber bundle 25 to the sample under test 24. Light reflected from sample under test 24 is reflected back through fiber bundle 25, then to imager 32 via beam splitter 27. Fiber bundle 25 can include one or more coherent optical fiber bundles. Light from light source 22 can be passed through an optional lens before the light enters fiber bundle 25. A lens can be located between light source 22 and beam splitter 27 and/or between beam splitter 27 and fiber bundle 25, and between fiber bundle 25 and sample under test 24.

Figure 4:
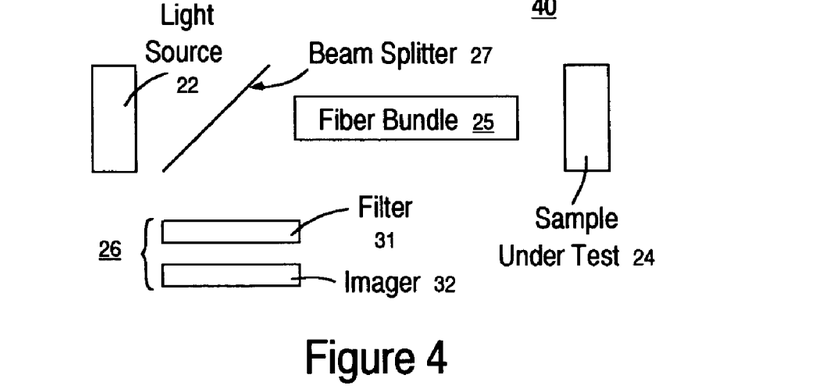
FIG. 4 is a block diagram of one embodiment of a reflective imaging system in accordance with the invention.

FIG. 4 is a block diagram of an apparatus 40 for en-face reflective imaging (not OCT) in one embodiment in accordance with the invention. In operation, apparatus 40 functions as follows for an example based on two wavelengths; however, the invention is not so limited. Light source 22 generates light having multiple wavelengths including a first wavelength and a second wavelength. The first and second wavelengths are selectable, as described above. The light may be filtered by an optional bulk filter as it is transmitted from light source 22 (e.g., a bulk filter such as that described by FIG. 8). The light from light source 22 also may be passed through an optional lens before reaching beam splitter 27 and/or before entering fiber bundle 25.

The light is transmitted through fiber bundle 25 to the sample under test 24, where it is reflected back through fiber bundle 25. Fiber bundle 25 can include one or more coherent optical fiber bundles.

Light reflected from the sample under test 24 is directed to imager 32 via beam splitter 27. The reflected light may be passed through an optional lens before reaching imager 32. The reflected light may be filtered by the optional filter 31 before the light reaches imager 32. Imager 32 distinguishes between reflected light at the first wavelength and reflected light at the second wavelength, as described further in conjunction with FIG. 7. Image data corresponding to the first wavelength and image data corresponding to the second wavelength can be used to generate one or more en-face images. For example, separate en-face images may be generated corresponding to the different wavelengths, or a single en-face image may be generated based on the combination of the image data (for example, as described below, image data may be differenced).

FIG. 4 illustrates an application in which the light source 22 and imager 32 are situated outside of the sample under test. Either or both the light source 22 and imager 32 could be situated within a body (e.g., on a tool such as an endoscope).

Figure 5:
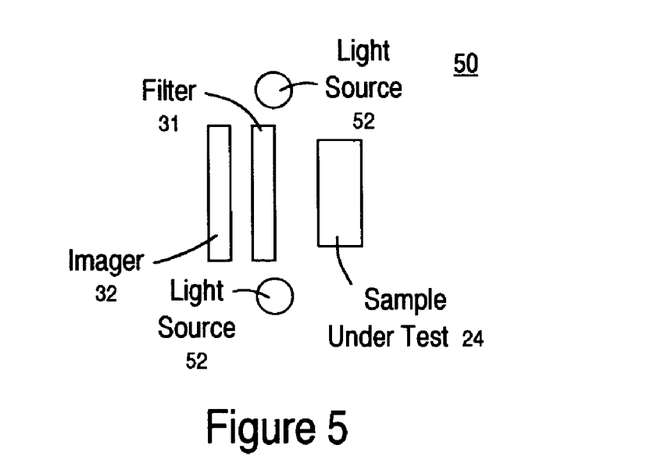
FIG. 5 is a block diagram of a second embodiment of a reflective imaging system in accordance with the invention.

FIG. 5 is a block diagram of an apparatus 50 for en-face reflective imaging (not OCT) in one embodiment in accordance with the invention. In operation, apparatus 50 functions as follows for an example based on two wavelengths; however, the invention is not so limited. Light sources 52 generate light having multiple wavelengths including a first wavelength and a second wavelength. Although light sources 52 is illustrated consisting of two light sources, the invention is not so limited. The first and second wavelengths are selectable, as described above. The light may be filtered by an optional bulk filter as it is transmitted from light sources 52.

Light reflected from the sample under test 24 is reflected onto imager 32. The reflected light may be filtered by the optional filter 31 before the light reaches imager 32. Imager 32 distinguishes between reflected light at the first wavelength and reflected light at the second wavelength, as described further in conjunction with FIG. 7. Image data corresponding to the first wavelength and image data corresponding to the second wavelength can be used to generate one or more en-face images. For example, separate en-face images may be generated corresponding to the different wavelengths, or a single en-face image may be generated based on the combination of the image data (for example, as described below, image data may be differenced).

FIG. 5 illustrates an application in which the light sources 52 and the imager 32 are situated outside of the sample under test. Either or both the light sources 52 and the imager 32 could be situated within a body (e.g., on a tool such as an endoscope).

Figure 6:
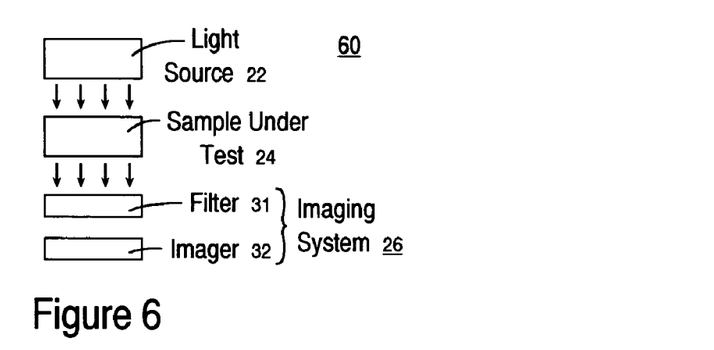
FIG. 6 is a block diagram of one embodiment of a transmissive imaging system in accordance with the invention.

FIG. 6 is a block diagram of an apparatus 60 for en-face transmissive imaging through a sample under test 24 in one embodiment in accordance with the invention. In operation, apparatus 60 functions as follows for an example based on two wavelengths; however, the invention is not so limited. Light source 22 generates light having multiple wavelengths including a first wavelength and a second wavelength. The first and second wavelengths are selectable, as described above. The light may be filtered by an optional bulk filter as it is transmitted from light source 22 (e.g., a bulk filter such as that described by FIG. 8). The light is essentially broadcast onto the sample under test 24.

The light is transmitted through the sample under test 24, where it is absorbed or attenuated by an amount depending on the characteristics of the material through which the light is passing. For example, the transmission of light at each wavelength is a function of the thickness, composition and structure of the skin, tissue, bone, blood and other material through which the light passes.

Continuing with reference to FIG. 6, light from the sample under test 24 is received by imager 32. The reflected light may be filtered by the optional filter 31 before the light reaches imager 32. Imager 32 distinguishes between reflected light at the first wavelength and reflected light at the second wavelength, as described further in conjunction with FIG. 7. Image data corresponding to the first wavelength and image data corresponding to the second wavelength can be used to generate one or more en-face images. For example, separate en-face images may be generated corresponding to the different wavelengths, or a single en-face image may be generated based on the combination of the image data (for example, as described below, image data may be differenced).

FIG. 6 illustrates an application in which the light source 22 and imager 32 are situated outside of the sample under test. Either or both the light source 22 and imager 32 could be situated within a body (e.g., on a tool such as an endoscope).

Figure 7:
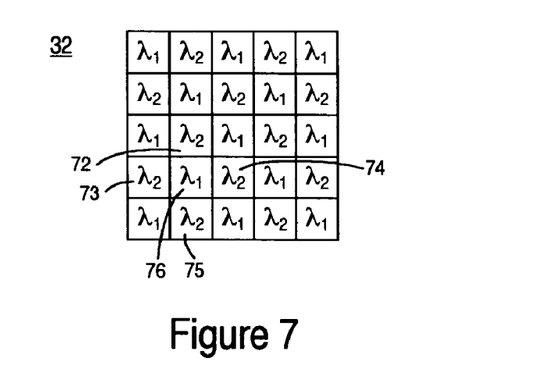
FIG. 7 illustrates one embodiment of an imager in accordance with the invention.

FIG. 7 illustrates an imager 32 in one embodiment in accordance with the invention. FIG. 7 illustrates an example in which two wavelengths ($\lambda_1$ and $\lambda_2$) and two types of filters are used. However, the invention is not so limited, and imager 32 can be configured for more than two wavelengths and/or more than two types of filters. Imager 32 is illustrated as a five-by-five array; however, the invention is not limited to those dimensions.

In the present embodiment, imager 32 includes a number of first regions and a number of second regions. The first regions are for detecting light of the first wavelength ($\lambda_1$) and the second regions are for detecting light of the second wavelength ($\lambda_2$). In one embodiment, the first regions include a filter material for blocking (filtering) light of the second wavelength, and the second regions include a filter material for blocking light of the first wavelength. Using two different filters, one for each wavelength, facilitates the detection of the different wavelengths; however, it is not necessary to use two different filters that perform as just described. That is, in an alternate embodiment, the first regions include a filter material for blocking (filtering) light of the second wavelength while detecting light of the first wavelength, while the second regions detect light of both wavelengths (that is, the second regions do not include a filter material for blocking light of the first wavelength).

In the embodiment of FIG. 7, a checkerboard pattern is formed on the surface of imager 32; however, other patterns of filter types/filter materials can be used. Patterns other than checkerboard patterns can be used, for example, when more than two types of filters are incorporated into imager 32. Patterns of filter types can be regular or irregular in nature. Also, the different regions of imager 32 (corresponding to the different types of filters and filter materials) are illustrated as being square in shape. However, the present invention is not so limited; that is, regular-shaped regions other than squares as well as irregular-shaped regions can be used. In one embodiment, each region corresponds to a respective pixel of the imager 32. For optical coherence tomography (OCT), pixel sensitivities and the excitation source are selected so that the wavelengths $\lambda_1$ and $\lambda_2$ are present in the spectrum of the light source.

Filters can be created as polymers doped with pigments or dyes, interference filters, reflective filters, or absorbing filters made of semiconductors, metals, other inorganic materials, or organic materials, created in any of a number of ways. Pigment-doped or dye-doped polymer filters (e.g., colored photoresists) provide an inexpensive solution. Direct deposition of organic pigments or dyes is also possible. Deposition of thin-film dielectric filters is another approach, with proper design so that the dielectric filters are not too thick compared to the lateral dimensions of the pixels. Deposition of semiconductor material with distinct band-edge behavior provides yet another approach.

The filter materials can be deposited (e.g., layered) as a separate layer of imager 32 (e.g., on top of an underlying layer) using conventional deposition and photolithography processes while still in wafer form, reducing the cost to manufacture. Additionally or alternatively, the filter materials may be mounted as separate elements between the imager 32 and incident light, allowing filtering of light before the light reaches the surface of imager 32. In yet another embodiment, the wavelength sensitivity may be varied within the silicon pixels themselves in a checkerboard pattern, for example.

Image data collected at two wavelengths can be differenced to compare the responses at the two wavelengths. An averaging technique can be applied before the wavelengths are differenced. In general, a signal value for a region can be computed for a particular wavelength using signal values from one or more neighboring regions at the same wavelength. For example, an average signal value for $\lambda_2$ can be determined for region 76 by averaging the $\lambda_2$ signal values for regions 72, 73, 74 and 75. The computed signal value for $\lambda_2$ at region 76 can be compared to the measured signal value for $\lambda_1$ at region 76.

Before processing (e.g., differencing) of the image data, gain factors can be applied to the signals generated from the different regions or pixels of imager 32 to account for any differences in sensitivity between the transmission characteristics of each region/pixel. Imager 32 can be used in combination with a bulk or large area filter (e.g., optional filter 31 of FIGS. 3–6), in which case the gain factors are determined considering the effect of filter 31 on the region-by-region (pixel-by-pixel) differences in sensitivity of imager 32.

The processing of image data as just described can be carried out rapidly using an on-board image processing chip, allowing rapid acquisition of successive en-face images. For contemporary imagers at video graphics array (VGA) resolution, collection rates of 15 frames per second are commonly achievable. Because adjacent regions (e.g., pixels) can be compared, image distortions due to bulk optic effects (e.g., barrel distortion) are minimized. With use of an averaging technique, signal values for the same region (e.g., pixel) can be compared, as described above.

Consider the example mentioned above, in which two wavelengths are selected to distinguish between oxyhemoglobin and hemoglobin without bound oxygen. Taking the difference between signal values for the two wavelengths can facilitate discrimination between regions of comparatively good and bad blood oxygenation. In other words, an en-face image can be generated based on the difference between the two sets of image data. Alternatively, an en-face image can be generated based on the set of image data corresponding to the first wavelength, and another en-face image can be generated based on the set of image data corresponding to the second wavelength.

Figure 8:
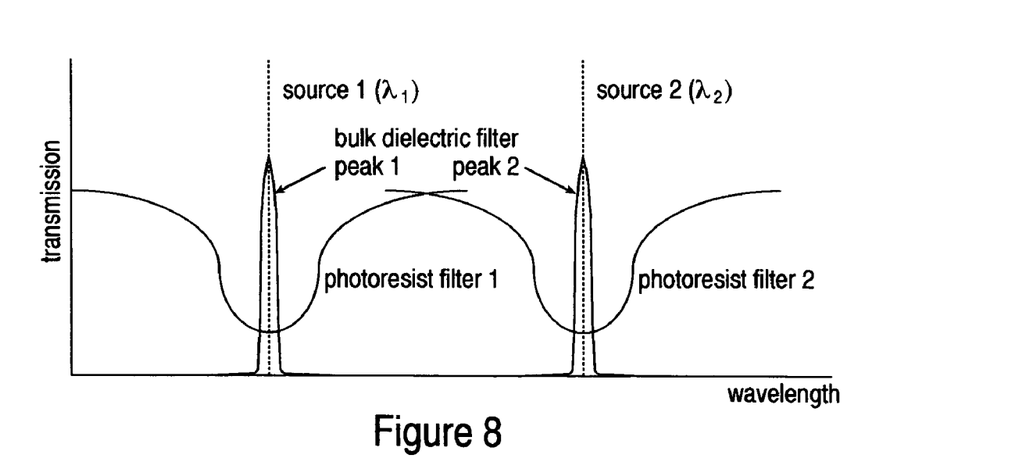
FIG. 8 is a graph illustrating transmission characteristics of different filters that can be used by embodiments in accordance with the invention.

FIG. 8 illustrates transmission versus wavelength characteristics of filter 31 and imager 32 (FIGS. 3–6) in accordance with the invention. As described in conjunction with FIG. 7 above, in the present embodiment, imager 32 includes a number of regions that block a band of light that includes light at a first wavelength and a number of other regions that block a band of light that includes light at a second wavelength. In the example of FIG. 8, imager 32 includes regions that include photoresist filter 1 material to block the band of light that includes light at the first wavelength ($\lambda_1$), and regions that include photoresist filter 2 material to block the band of light that includes light at the second wavelength ($\lambda_2$).

Filter 31 includes one or more materials that serve to transmit light only within a narrow wavelength band or bands. In the example of FIG. 8, the filter 31 transmits light in relatively narrow bands (peak 1 and peak 2) around the selected first and second wavelengths ($\lambda_1$ and $\lambda_2$, respectively), blocking or reducing light of wavelengths outside the band. In other words, only light in the relatively narrow bands around the first and second wavelengths passes through filter 31 to imager 32. However, the bands are not so narrow as to degrade the depth resolution. Accordingly, the detection of the first and second wavelengths by imager 32 is facilitated.

Bulk interference filters commonly transmit integral subharmonics of the chosen wavelength. For example, a filter designed to transmit 800 nm wavelength light will also transmit 400 nm wavelength light. Order-sorting filters can be used as part of the filter 31 to filter out light at wavelengths that are subharmonics of the first and second wavelengths. A filter that blocks out light below 800 nm (e.g., a filter with a threshold of 600 nm) can be used to block light at the subharmonic wavelengths.

Figure 9:
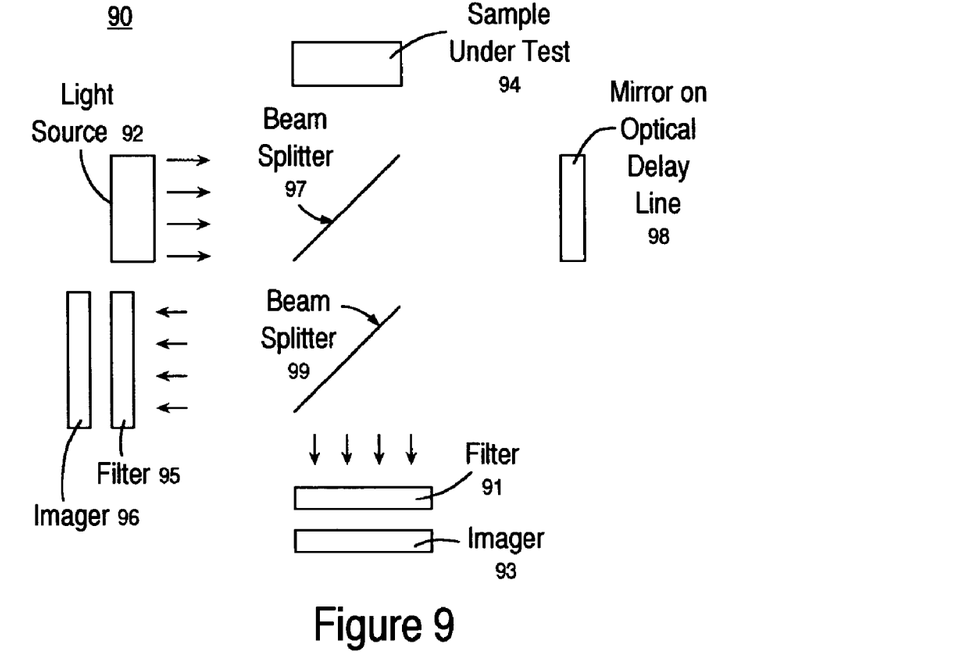
FIG. 9 is a block diagram of another embodiment of an en-face imaging system in accordance with the invention.

FIG. 9 is a block diagram of an apparatus 90 for en-face imaging in one embodiment in accordance with the invention. Relative to apparatus 30 of FIG. 3, for example, apparatus 90 includes a second beam splitter 99 and at least two imagers: first imager 93 and second imager 96. The second beam splitter 99 can be a 50/50 beam splitter or a dichroic beam splitter. The first imager 93 is for detecting light of a first wavelength, and the second imager 96 is for detecting light of a second wavelength.

Filters 91 and 95 are optionally included in apparatus 90. For example, if the second beam splitter 99 is a dichroic beam splitter, then filters 91 and 95 may or may not be used. If the second beam splitter 99 is a 50/50 beam splitter, then filter 91 can be used to block light of the second wavelength from reaching the first imager 93, and filter 95 can be used to block light of the first wavelength from reaching the second imager 96.

In operation, apparatus 90 of FIG. 9 functions as follows for an example based on two wavelengths; however, the invention is not so limited. Light source 92 generates light having a first and second wavelength. The first and second wavelengths are selectable, as described previously herein. The light transmitted by light source 92 may be filtered by an optional bulk filter (e.g., a bulk filter such as that described by FIG. 8). A bulk filter such as that described by FIG. 8 can optionally be placed in other locations within apparatus 90, for example, before beam splitter 99.

Continuing with reference to FIG. 9, a portion of the light from light source 92 is directed to sample under test 94 by beam splitter 97, and the remainder of the light is passed to mirror on optical delay line 98. The light is essentially broadcast to the sample under test 94 and the mirror on optical delay line 98 in free space, although some or all of the free space portions of apparatus 90 can instead be fiber-based.

Light reflected from the sample under test 94 and from mirror on optical delay line 98 is received by beam splitter 99. If beam splitter 99 is a 50/50 beam splitter, half of the reflected light from the sample is directed to the first imager 93 and the remainder of the reflected light is directed to the second imager 96. Filter 91 can be used to block light of the second wavelength from reaching the first imager 93, and filter 95 can be used to block light of the first wavelength from reaching the second imager 96. If beam splitter 99 is a dichroic beam splitter, then one wavelength (e.g., the second wavelength) would be reflected to second imager 96 and other wavelength (e.g., the first wavelength) would be transmitted to first imager 93.

First imager 93 detects light of the first wavelength, and second imager 96 detects light of the second wavelength. Image data corresponding to the first wavelength and image data corresponding to the second wavelength can then be used to generate one or more en-face images. Image data generated by the two imagers can be differenced. As separate imagers, the first imager 93 and the second imager 96 are registered spatially and synchronized temporally to capture images at the different wavelengths simultaneously.

Figure 10:
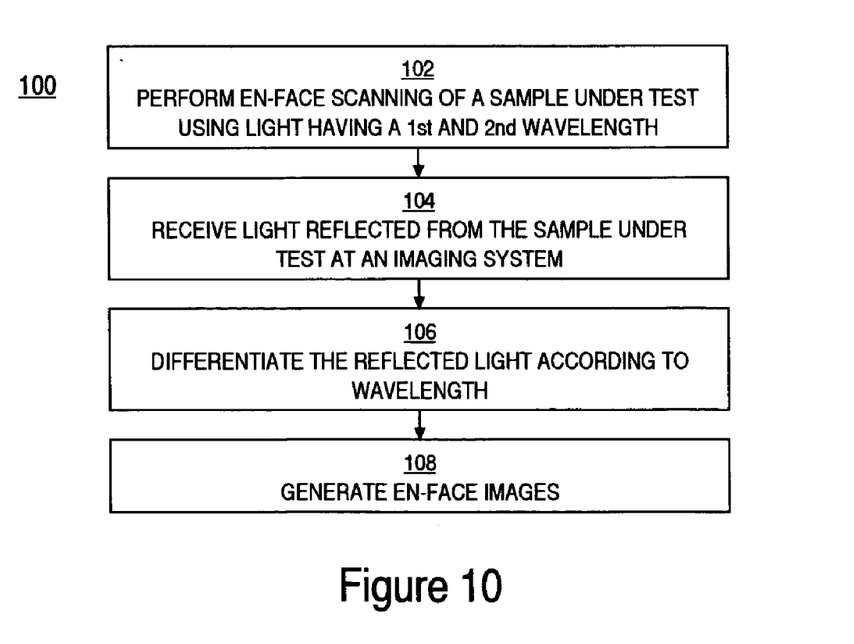
FIG. 10 is a flowchart of an embodiment of a method for en-face imaging using multiple wavelengths in accordance with the invention.

FIG. 10 is a flowchart 100 of a method for en-face imaging using multiple wavelengths in one embodiment in accordance with the invention. Although specific steps are disclosed in flowchart 100, such steps are exemplary. That is, embodiments in accordance with the invention are well suited to performing various other steps or variations of the steps recited in flowchart 100. It is appreciated that the steps in flowchart 100 may be performed in an order different than presented, and that not all of the steps in flowchart 100 may be performed.

In step 102, en-face images are captured of a sample under test using light that has at least a first and second wavelength. The wavelengths to be used for the en-face scanning and imaging can be selected according to the application, the nature of the information that is being collected, the nature of the subject under test, and other factors. The source of light can be a broadband source, having wavelengths other than selected wavelengths. In one embodiment, light transmitted from the light source is filtered to eliminate wavelengths outside the relatively narrow band of the selected wavelengths.

In step 104, light reflected from the sample under test is received in an imaging system that includes a single imager such as imager 32 of FIGS. 3–6, or multiple imagers such as imagers 93 and 96 of FIG. 9. The reflected light may be filtered before it reaches the imagers.

In step 106 of FIG. 10, reflected light corresponding to the first wavelength and reflected light corresponding to the second wavelength are separated from each other. That is, for example, an imager such as imager 32 (FIGS. 3–6) can have regions for detecting reflected light at the first wavelength and other regions for detecting reflected light at the second wavelength. Alternatively, a first imager (e.g., imager 93 of FIG. 9) serves to detect reflected light at the first wavelength and a second imager (e.g., imager 96 of FIG. 9) serves to detect light at the second wavelength.

In step 108 of FIG. 10, en-face images are output based on the image data generated by the imager or imagers. Separate en-face images can be output for each wavelength in use. Alternatively, the image data for the different wavelengths can be differenced, and the difference between the sets of image data can be used to generate an en-face image.

The process just described is repeated to obtain en-face images at different depths of the sample under test.

In summary, embodiments in accordance with the invention allow the rapid collection of en-face data by using a two-dimensional imager. Contrast is increased by providing the capability for simultaneously imaging at multiple wavelengths. Using coherent fiber bundles, in vivo as well as in vitro measurements can be performed.

The multiple wavelength en-face imagers described herein can be used in a variety of applications, including medical imaging and measurement applications as part of OCT or endoscopy. Medical imaging applications include coronary and vascular imaging, oncology, dentistry, neurosurgery, gastroenterology, otolaryngology, dermatology, ophthalmology, thoracic surgery, urology, and orthopedics. Measurement applications include cell imaging and metrology in manufacturing.

Embodiments in accordance with the invention can be particularly advantageous when fluorescent tags are being used. Conventionally, a patient is injected with a fluorescent medium (e.g., a fluorescent dye) that will attach itself to cancerous cells, for example. Using multiple (e.g., two) wavelengths and an en-face imaging system as described herein, it is not necessary to take a "before" image, inject the dye and wait for the dye to take effect, and then take an "after" image. Instead, the dye can be injected and, after the dye has taken effect, simultaneous images can be taken using one wavelength that excites the dye fluorescence and another wavelength that does not excite the fluorescence of that particular dye. Differencing of the images can then be performed to highlight regions in the sample under test that fluoresced. Conventionally, the patient may be subject to a degree of discomfort and perhaps a degree of risk (e.g., if the patient is anesthetized) while waiting for the dye to take effect. Also during that time, the imaging device or the patient may move slightly, causing the before and after images to be offset. By taking simultaneous images in accordance with the invention, these problems are overcome.

The invention is thus described in various embodiments. While the invention has been described in particular embodiments, it should be appreciated that the invention should not be construed as limited by such embodiments, but rather construed according to the following claims.

What is claimed is:

1. An apparatus for medical imaging or manufacturing process control using multiple wavelength detection, said apparatus comprising:
    a light source operable to produce light at different wavelengths, said light directed at a sample under test; and
    an imager operable for detecting light from said sample under test, said imager comprising a plurality of first regions, said plurality of first regions comprising a filter material for detecting light that comprises light at a first wavelength while blocking light that comprises light at a second wavelength, said imager further comprising a plurality of second regions, said plurality of second regions comprising a filter material for detecting light comprising light at said second wavelength, wherein said first and second regions each corresponds to a respective pixel of said first imager and wherein said first regions and said second regions are interleaved in a pattern, and wherein a signal value corresponding to said second wavelength is determined for a first region using signal values from a subset of said second regions neighboring said first region.

2. The apparatus of claim 1 wherein said second regions comprise a filter material for blocking light that comprises light at said first wavelength.

3. The apparatus of claim 1 wherein said pattern comprises a regular pattern of said first and second regions.

4. The apparatus of claim 1 wherein en-face images are output using en-face image data corresponding to said first wavelength and en-face image data corresponding to said second wavelength.

5. The apparatus of claim 4 wherein said en-face image data corresponding to said first wavelength and said en-face image data corresponding to said second wavelength are differenced.

6. The apparatus of claim 1 wherein gain factors are selectively applied to said first and second regions.

7. The apparatus of claim 1 further comprising a filter for blocking light having a wavelength other than said first and second wavelengths.

8. The apparatus of claim 7 further comprising a filter for blocking subharmonics of said first and second wavelengths.

9. The apparatus of claim 1 wherein said light source comprises a source of white light and a diffuser.

10. The apparatus of claim 1 used for optical coherence tomography.

11. An apparatus for en-face imaging using multiple wavelengths, said apparatus comprising:
    an interferometer adapted for en-face image capturing of a sample under test using light having multiple wavelengths including a first wavelength and a second wavelength;
    a plurality of first elements optically coupled to said interferometer, said first elements operable for receiving light reflected from said sample under test and for detecting reflected light comprising light of said first wavelength but not light of said second wavelength; and
    a plurality of second elements optically coupled to said interferometer, said second elements operable for receiving light reflected from said sample under test and for detecting reflected light comprising light of said second wavelength, wherein said first and second elements are interleaved in a single imager, and wherein signal values from a subset of said second elements neighboring a first element are averaged to determine a signal value corresponding to said second wavelength for said first element;
    wherein en-face images are output using en-face image data corresponding to said first wavelength and en-face image data corresponding to said second wavelength.

12. The apparatus of claim 11 wherein said first elements comprise a filter material for blocking light of said second wavelength.

13. The apparatus of claim 12 wherein said second elements comprise a filter material for blocking light of said first wavelength.

14. The apparatus of claim 11 wherein each of said first and second elements corresponds to a respective pixel of said imager.

15. The apparatus of claim 11 further comprising a filter for blocking light comprising a wavelength other than said first and second wavelengths.

16. The apparatus of claim 11 wherein said en-face image data corresponding to said first wavelength and said en-face image data corresponding to said second wavelength are differenced.

17. The apparatus of claim 11 wherein said interferometer comprises an optical fiber bundle.

18. A method for en-face imaging using multiple wavelengths, said method comprising:
   capturing en-face images of a sample under test using light having multiple wavelengths including a first wavelength and a second wavelength;
   receiving light reflected from said sample under test and distinguishing between reflected light corresponding to said first wavelength and reflected light corresponding to said second wavelength using an imager comprising interleaved first regions and second regions, said first regions for detecting light of said first wavelength and said second regions for detecting light of said second wavelength;
   determining a signal value for said second wavelength for a first region using signal values from a subset of said second regions neighboring said first region; and
   outputting en-face images using en-face image data corresponding to said first wavelength and en-face image data corresponding to said second wavelength.

19. The method of claim 18 further comprising:
applying gain factors to selected first regions and selected second regions.

20. The method of claim 18 further comprising:
determining a difference between said en-face image data corresponding to said first wavelength and said en-face image data corresponding to said second wavelength.

21. The method of claim 18 further comprising:
blocking light having a wavelength other than said first and second wavelengths.

\* \* \* \* \*